(12) United States Patent
Jeppesen et al.

(10) Patent No.: US 7,067,530 B2
(45) Date of Patent: Jun. 27, 2006

(54) COMPOUNDS, THEIR PREPARATION AND USE

(75) Inventors: Lone Jeppesen, Virum (DK); Paul Stanley Bury, Lancashire (GB); John Patrick Mogensen, Herlev (DK); Ingrid Pettersson, Frederiksberg (DK); Per Sauerberg, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/217,595

(22) Filed: Jul. 29, 2002

(65) Prior Publication Data

US 2003/0109560 A1 Jun. 12, 2003

Related U.S. Application Data

(60) Provisional application No. 60/309,951, filed on Aug. 3, 2001.

(30) Foreign Application Priority Data

Jul. 30, 2001 (DK) .......................... PA 2001 01151

(51) Int. Cl.
*C07D 215/14* (2006.01)
*A61K 31/47* (2006.01)

(52) U.S. Cl. ...................... 514/311; 546/174; 562/452; 562/433; 562/405

(58) Field of Classification Search ................ 514/311; 546/174; 562/452, 433, 405
See application file for complete search history.

(56) References Cited

U.S. PATENT DOCUMENTS 5,306,726 A 4/1994 Hulin .......................... 514/375

FOREIGN PATENT DOCUMENTS

| EP | 0098690 A2 | 1/1984 |
| EP | 1167357 A1 | 1/2002 |
| WO | WO 91/19702 | 12/1991 |
| WO | WO 94/01420 | 1/1994 |
| WO | WO 99/19313 | 4/1994 |
| WO | WO 94/13650 | 6/1994 |
| WO | WO 94/29285 | 12/1994 |
| WO | WO 95/03038 | 2/1995 |
| WO | WO 95/17394 | 6/1995 |
| WO | WO 96/04260 | 2/1996 |
| WO | WO 97/25042 | 7/1997 |
| WO | WO 97/31907 | 9/1997 |
| WO | WO 97/36579 | 10/1997 |
| WO | WO 99/08501 | 2/1999 |
| WO | WO 99/16758 | 4/1999 |
| WO | WO 00/63153 | 10/2000 |
| WO | WO 01/00603 A1 | 1/2001 |
| WO | WO 01/55085 A1 | 8/2001 |

OTHER PUBLICATIONS

Collins, J Med Chem, vol. 41, pp. 5037-5054, 1998.*
Sorbera et al., Drugs of the Future 2001, vol. 26, No. 4, pp. 354-363.
Brown et al., Diabetes, vol. 48, pp. 1415-1424 (1999).
Henke et al., J. Med. Chem, vol. 41, pp. 5020-5036 (1998).
Collins et al., Journal of Medicinal Chemistry, vol. 41, No. 25, pp. 5037-5054 (1998).
Cobb et al., J. Med. Chem., vol. 41, pp. 5055-5069 (1998).
Abstract of Patent No. WO 97/43241.
Berger et al., The Journal of Biological Chemistry, vol. 274, No. 10, pp. 6718-6725 (1999).
Leibowitz, FEBS Letters, vol. 473, pp. 333-336 (2000).
Oliver et al., PNAS. vol. 98, No. 9, pp. 5306-5311 (2001).
Davis et al., Tetrahedron, vol. 55, pp. 11653-11667 (1999).

* cited by examiner

*Primary Examiner*—D. Margaret Seaman
(74) *Attorney, Agent, or Firm*—Rosemarie R. Wilk-Orescan; Reza Green; Richard W. Bork

(57) ABSTRACT

Novel compounds of general formula (I), the use of these compounds as medicaments, pharmaceuticaly compositions comprising the compounds and methods of treatment employing these compounds and compostiones. The present compounds may be useful in the treatment and/or prevention of conditions mediated by nuclear receptors, in particular the Peroxisome Proliferator-Activated Receptors (PPAR). The compounds exert their effects by modulating the PPARγ response in a partial agonist manner.

21 Claims, No Drawings

COMPOUNDS, THEIR PREPARATION AND USE

This application claims the benefit of Provisional application Ser. No. 60/309,951, filed Aug. 3, 2001.

FIELD OF THE INVENTION

The present invention relates to novel vinyl N-(2-benzoylphenyl)-L tyrosine derivatives, to the use of these compounds as pharmaceutical compositions, to pharmaceutical compositions comprising the compounds and to a method of treatment employing these compounds and compositions. More specifically, the compounds of the invention can be utilised in the treatment and/or prevention of conditions mediated by the Peroxisome Proliferator-Activated Receptors (PPAR). The compounds exert their effects by modulating the PPARγ response in a partial agonist manner.

BACKGROUND OF THE INVENTION

Coronary artery disease (CAD) is the major cause of death in Type 2 diabetic and metabolic syndrome patients (i.e. patients that fall within the 'deadly quartet' category of impaired glucose tolerance, insulin resistance, hypertriglyceridaemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in Type 2 diabetic or metabolic syndrome patients. The thiazolidinediones also potently lower circulating glucose levels of Type 2 diabetic animal models and humans. However, the fibrate class of compounds are without beneficial effects on glycaemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialised proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarised as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty acid β-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

PPARδ activation was initially reported not to be involved in modulation of glucose or triglyceride levels. (Berger et al., j. Biol. Chem., 1999, Vol 274, pp. 6718–6725). Later it has been shown that PPARδ activation leads to increased levels of HDL cholesterol in dbldb mice (Leibowitz et al. FEBS letters 2000, 473, 333–336). Further, a PPARδ agonist when dosed to insulin-resistant middle-aged obese rhesus monkeys caused a dramitic dose-dependent rise in serum HDL cholesterol while lowering the levels of small dense LDL, fasting triglycerides and fasting insulin (Oliver et al. PNAS 2001, 98, 5306–5311).The same paper also showed that PPARδ activation increased the reverse cholesterol transporter ATP-binding cassette A1 and induced apolipoprotein A1-specific cholesterol efflux. Taken together these observations suggest that PPARδ activation is useful in the treatment and prevention of cardiovascular diseases and conditions including atherosclerosis, hypertriglyceridemia, and mixed dyslipidaemia (PCT publication WO 01/00603 (Chao et al.).

A number of compounds have been reported to be useful in the treatment of hyperglycemia, hyperlipidemia and hypercholesterolemia (U.S. Pat. No. 5,306,726, PCT Publications nos. WO91/19702, WO 95/03038, WO 96/04260, WO 94/13650, WO 94/01420, WO 97/36579, WO 97/25042, WO 95/17394, WO 99/08501, WO 99/19313, WO 99/16758 and WO 01/00603).

Glucose lowering as a single approach does not overcome the macrovascular complications associated with Type 2 diabetes and metabolic syndrome. Novel treatments of Type 2 diabetes and metabolic syndrome must therefore aim at lowering both the overt hypertriglyceridaemia associated with these syndromes as well as alleviation of hyperglycaemia.

This indicate that research for compounds displaying various degree of PPARα, PPARγ and PPARδ activation should lead to the discovery of efficacious triglyceride and/or cholesterol and/or glucose lowering drugs that have great potential in the treatment of diseases such as type 2 diabetes, dyslipidemia, syndrome X (including the metabolic syndrome, i.e. impaired glucose tolerance, insulin resistance, hypertrigyceridaemia and/or obesity), cardiovascular diseases (including atherosclerosis) and hypercholesteremia.

Clinically available PPARγ agonists (rosiglitazone and pioglitazone) are full agonists, which lower blood glucose and improve insulin resistance in type 2 diabetic patients, but at the same time it has been reported that they also induce body weight gain, anaemia and oedema limiting the utility of such compounds.

N-(2-benzoylphenyl)-L tyrosine derivatives have been described in Henkel et al. *J. Med Chem.* (1998), 41(25), 5020–5036, Collins et al. *J. Med Chem.* (1998), 41(25), 5037–5054, Cobb et al. *J. Med Chem.* (1998), 41(25), 5055–5069, Davis et al. *Tetrahedron* (1999), 55(39), 11653–11668, WO 9429285, and also in WO 9731907 wherein the derivatives are described as being potent and selective PPARγ agonists.

The present invention relates to vinyl N-(2-benzoylphenyl)-L tyrosine derivatives displaying partial PPARγ agonist activity as well as various degree of PPARα agonist activity.

DEFINITIONS

In the structural formulas given herein and throughout the present specification the following terms have the indicated meaning:

The term "$C_{1-6}$-alkyl" as used herein, alone or in combination, represent a linear or branched, saturated hydrocarbon chain having the indicated number of carbon atoms. Examples of such groups include, but are not limited to methyl, ethyl, n-propyl, isopropyl, butyl, isobutyl, sec-butyl, tert-butyl, pentyl, isopentyl, hexyl, isohexyl and the like.

The term "$C_{3-6}$-cycloalkyl" as used herein, alone or in combination, represent a saturated monocyclic hydrocarbon group having the indicated number of carbon atoms. Examples of such groups include, but are not limited to cyclopropyl, cyclobutyl, cyclopentyl, cyclohexyl and the like.

The term "$C_{2-6}$-alkenyl" as used herein, represent an olefinically unsaturated branched or straight hydrocarbon group having from 2 to the specified number of carbon atoms and at least one double bond. Examples of such groups include, but are not limited to, vinyl, 1-propenyl, 2-propenyl, allyl, iso-propenyl, 1,3-butadienyl, 1-butenyl, hexenyl, pentenyl and the like.

The term "$C_{2-6}$-alkynyl" as used herein, represent an unsaturated branched or straight hydrocarbon group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The term "$C_{1-6}$-alkoxy" as used herein, alone or in combination, refers to a straight or branched configuration linked through an ether oxygen having its free valence bond from the ether oxygen. Examples of linear alkoxy groups are methoxy, ethoxy, propoxy, butoxy, pentoxy, hexoxy and the like. Examples of branched alkoxy are isopropoxy, sec-butoxy, tert-butoxy, isopentyloxy, isohexyloxy and the like.

The term "$C_{3-6}$-cycloalkoxy" as used herein, alone or in combination, represent a saturated monocyclic hydrocarbon group having the indicated number of carbon atoms linked through an ether oxygen having its free valence bond from the ether oxygen. Examples of cycloalkoxy groups are cyclopropyloxy, cyclobutyloxy, cyclopentyloxy, cyclohexyloxy and the like.

The term "$C_{1-6}$-alkylthio" as used herein, alone or in combination, refers to a straight or branched monovalent substituent comprising a $C_{1-6}$-alkyl group linked through a divalent sulfur atom having its free valence bond from the sulfur atom and having 1 to 6 carbon atoms e.g. methylthio, ethylthio, propylthio, butylthio, pentylthio and the like.

The term "$C_{3-6}$-cycloalkylthio" as used herein, alone or in combination, represent a saturated monocyclic hydrocarbon group having the indicated number of carbon atoms linked through a divalent sulfur atom having its free valence bond from the sulfur atom. Examples of cycloalkoxy groups are cyclopropylthio, cyclobutylthio, cyclopentylthio, cyclohexylthio and the like.

The term "$C_{1-6}$-alkylamino" as used herein, alone or in combination, refers to a straight or branched monovalent substituent comprising a $C_{1-6}$-alkyl group linked through amino having a free valence bond from the nitrogen atom e.g. methylamino, ethylamino, propylamino, butylamino, pentylamino and the like.

The term "$C_{3-6}$-cycloalkylamino" as used herein, alone or in combination, represent a saturated monocyclic hydrocarbon group having the indicated number of carbon atoms linked through amino having a free valence bond from the nitrogen atom e.g. cyclopropylamino, cyclobutylamino, cyclopentylamino, cyclohexylamino and the like.

The term "aryl" as used herein refers to an aromatic monocyclic or an aromatic fused bi- or tricyclic hydrocarbon group e.g. phenyl, naphthyl, anthracenyl, phenanthrenyl, azulenyl and the like.

The term "halogen" means fluorine, chlorine, bromine or iodine.

The term "perhalomethyl" means trifluoromethyl, trichloromethyl, tribromomethyl or triiodomethyl.

The term "perhalomethoxy" means trifluoromethoxy, trichloromethoxy, tribromomethoxy or triiodomethoxy.

The term "$C_{1-6}$-dialkylamino" as used herein refers to an amino group wherein the two hydrogen atoms independently are substituted with a straight or branched, saturated hydrocarbon chain having the indicated number of carbon atoms; such as dimethylamino, N-ethyl-N-methylamino, diethylamino, dipropylamino, N-(n-butyl)-N-methylamino, di(n-pentyl)amino and the like.

The term "acyl" as used herein refers to a monovalent substituent comprising a $C_{1-6}$-alkyl group linked through a carbonyl group; such as e.g. acetyl, propionyl, butyryl, isobutyryl, pivaloyl, valeryl and the like.

The term "heteroaryl" as used herein, alone or in combination, refers to a monovalent substituent comprising a 5–7 membered monocyclic aromatic system or a 8–10 membered bicyclic aromatic system or a 12–16 membered tricyclic containing one or more heteroatoms selected from nitrogen, oxygen and sulfur, e.g. furyl, thienyl, pyrrolyl, imidazolyl, pyrazolyl, triazolyl, pyrazinyl, pyrimidinyl, pyridazinyl, isothiazolyl, isoxazolyl, oxazolyl, oxadiazolyl, thiadiazolyl, quinolyl, isoquinolyl, quinazolinyl, quinoxalinnyl, indolyl, benzimidazolyl, benzofuranyl, pteridinyl, purinyl, carbazolyl, phenazinyl, phenanthrolinyl, phenothiazinyl, phenoxazinyl and the like.

The term "heteroaryloxy" as used herein, alone or in combination, refers to a heteroaryl as defined herein linked to an oxygen atom having its free valence bond from the oxygen atom e.g. pyrrolyloxy, imidazolyloxy, pyrazolyloxy, triazolyloxy, pyrazinyloxy, pyrimidinyloxy, pyridazinyloxy, isothiazolyloxy, isoxazolyloxy, oxazolyloxy, oxadiazolyloxy, thiadiazolyloxy, quinolinyloxy, isoquinolinyloxy, quinazolinyloxy, quinoxalinyloxy, indoltloxy, benzimidazolyloxy, benzofuranyloxy, pteridinyloxy and purinyloxy carbazolyloxy, phenazinyloxy, phenanthrolinyloxy, phenothiazinyloxy, phenoxazinyloxy and the like.

The term "aralkyl" as used herein refers to a straight or branched saturated carbon chain containing from 1 to 6 carbons substituted with an aromatic carbohydride; such as benzyl, phenethyl, 3-phenylpropyl, 1-naphthylmethyl, 2-(1-naphthyl)ethyl and the like.

The term "aryloxy" as used herein refers to phenoxy, 1-naphthyloxy, 2-naphthyloxy and the like.

The term "aralkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "heteroaralkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "heteroaralkoxy" as used herein refers to a heteroarylalkyl as defined herein linked to an oxygen atom having its free valence bond from the oxygen atom, e.g. (2-furyl)methyl, (3-furyl)methyl, (2-thienyl)methyl, (3-thienyl)methyl, (2-pyridyl)methyl, 1-methyl-1-(2-pyrimidyl)ethyl linked to oxygen, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyl)-thio, (2-chlorophenyl)thio and the like.

The term "a fused polycyclic hydrocarbon" as used herein, alone or in combinations, refers to a polycyclic hydrocarbon, containing two ore more fused hydrocarbon rings, e.g. pentalene, indene, naphthalene, azulene, heptalene, biphenylene, fluorene, phenenthrene, antracene, and the like.

As used herein the term. "treatment" includes treatment, prevention and management of such condition.

Certain of the above defined terms may occur more than once in the above formula (I), and upon such occurrence each term shall be defined independently of the other.

DESCRIPTION OF THE INVENTION

The present invention relates to compounds of the general formula (I):

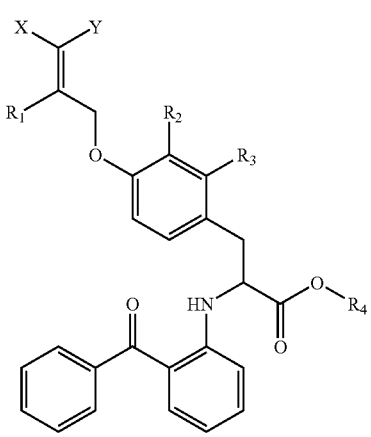

(I)

wherein X is biphenyl, a fused polycyclic hydrocarbon or heteroaryl each of which is optionally substituted with one or more substituents selected from halogen, perhalomethyl, perhalomethoxy, hydroxy, cyano, amino, $C_{1-6}$-alkylamino, $C_{3-6}$-cycloalkylamino, $C_{1-6}$-dialkylamino or carboxy; or $C_{1-6}$-alkyl, $C_{3-6}$-cycloalkyl, $C_{2-6}$-alkenyl, $C_{2-6}$-alkynyl, $C_{1-6}$-alkoxy, $C_{3-6}$-cycloalkoxy, $C_{1-6}$-alkylthio, $C_{3-6}$-cycloalkylthio each of which is optionally substituted with halogen; or aryl, aryloxy, arylthio, acyl, aralkyl, aralkoxy, heteroaryl, heteroaralkyl, heteroaryloxy, heteroaralkoxy each of which is optionally substituted with halogen, perhalomethyl or perhalomethoxy; and Y is aryl or heteroaryl each of which is optionally substituted with one or more substituents selected from halogen, perhalomethyl, perhalomethoxy, hydroxy, cyano, amino, $C_{1-6}$-alkylamino, $C_{3-6}$-cycloalkylamino, $C_{1-6}$-dialkylamino, carboxy or $C_{1-6}$-alkylester; or $C_{1-6}$-alkyl, $C_{3-6}$-cycloalkyl, $C_{3-6}$-cycloalkoxy, $C_{2-6}$-alkenyl, $C_{2-6}$-alkynyl, $C_{1-6}$-alkoxy, $C_{1-6}$-alkylthio, $C_{3-6}$-cycloalkylthio each of which is optionally substituted with halogen; or aryl, aryloxy, arylthio, acyl, aralkyl, aralkoxy, heteroaryl, heteroaralkyl, heteroaryloxy, heteroaralkoxy each of which is optionally substituted with halogen, perhalomethyl or perhalomethoxy; or Y is H, $C_{1-6}$-alkyl, $C_{3-6}$-cycloalkyl, $C_{2-6}$-alkenyl, $C_{2-6}$-alkynyl, $C_{4-6}$-alkenynyl; and $R_1$ is hydrogen or halogen; or $R_1$ is $C_{1-6}$-alkyl, $C_{3-6}$-cycloalkyl, $C_{1-6}$-alkoxy or $C_{3-6}$-cycloalkoxy each of which is optionally substituted with one or more substituents selected from halogen, hydroxy or cyano; and $R_2$ and $R_3$ are independently hydrogen, halogen, $C_{1-6}$-alkyl or $C_{3-6}$-cycloalkyl; and $R_4$ is hydrogen, $C_{1-6}$-alkyl or $C_{3-6}$-cycloalkyl; or a pharmaceutically acceptable salt thereof, or a pharmaceutically acceptable solvate thereof, or any tautomeric forms, stereoisomers, mixture of stereoisomers including a racemic mixture, or polymorphs.

In one embodiment, the present invention is concerned with compounds of formula (I) wherein X is biphenyl, a fused polycyclic hydrocarbon or heteroaryl each of which is optionally substituted with one or more substituents selected from halogen; or $C_{1-6}$-alkyl or $C_{1-6}$-alkoxy each of which is optionally substituted with halogen.

In another embodiment, the present invention is concerned with compounds of formula (I) wherein X is biphenyl optionally substituted with one or more substituents selected from halogen; or $C_{1-6}$-alkyl or $C_{1-6}$-alkoxy each of which is optionally substituted with halogen.

In another embodiment, the present invention is concerned with compounds of formula (I) wherein X is a fused polycyclic hydrocarbon optionally substituted with one or more substituents selected from halogen; or $C_{1-6}$-alkyl or $C_{1-6}$-alkoxy each of which is optionally substituted with halogen.

In another embodiment, the present invention is concerned with compounds of formula (I) wherein X is heteroaryl optionally substituted with one or more substituents selected from halogen; or $C_{1-6}$-alkyl or $C_{1-6}$-alkoxy each of which is optionally substituted with halogen.

In another embodiment, the present invention is concerned with compounds of formula (I) wherein X is biphenyl.

In another embodiment, the present invention is concerned with compounds of formula (I) wherein X is fluorenyl.

In another embodiment, the present invention is concerned with compounds of formula (I) wherein X is quinolyl.

In another embodiment, the present invention is concerned with compounds of formula (I) wherein Y is H.

In another embodiment, the present invention is concerned with compounds of formula (I) wherein Y is $C_{1-6}$-alkyl wherein Y is optionally substituted with one or more halogens.

In another embodiment, the present invention is concerned with compounds of formula (I) wherein $R_1$ is H or $C_{1-6}$-alkyl.

In another embodiment, the present invention is concerned with compounds of formula (I) wherein $R_2$ is hydrogen.

In another embodiment, the present invention is concerned with compounds of formula (I) wherein $R_3$ is hydrogen.

In another embodiment, the present invention is concerned with compounds of formula (I) wherein $R_4$ is hydrogen or $C_{1-6}$-alkyl.

In another embodiment, the present invention is concerned with compounds of formula (I) wherein $R_4$ is hydrogen or methyl.

In another embodiment, the present invention is concerned with compounds of formula (I), which are PPARγ agonist.

In another embodiment, the present invention is concerned with compounds of formula (I), which are partial PPAR agonist.

Examples of specific compounds of the invention are:

(E)-(S)-2-(2-Benzoyl-phenylamino)-3-[4-(3-biphenyl-4-yl-allyloxy)-phenyl]-propionic acid methyl ester, (E)-(S)-2-(2-Benzoyl-phenylamino)-3-[4-(3-biphenyl-4-yl-allyloxy)-phenyl]-propionic acid, (E)-(S)-2-(2-Benzoyl-phenylamino)-3-{4-[3-(9H-fluoren-2-yl)-allyloxyl]-phenyl}-propionic acid methyl ester, (E)-(S)-2-(2-Benzoyl-phenylamino)-3-{4-[3-(9H-fluoren-2-yl)-allyloxyl]-phenyl}-propionic acid, (S)-2-(2-Benzoyl-phenylamino)-3-{4-[2-ethyl-3-(9H-fluoren-2-yl)-allyloxy]-phenyl}-propionic acid methyl ester, (S)-2-(2-Benzoyl-phenylamino)-3-{4-[2-ethyl-3-(9H-fluoren-2-yl)-allyloxy]-phenyl}-propionic acid, (E)-(S)-2-(2-Benzoyl-phenylamino)-3-[4-(3-quinolin-2-yl-allyloxy)-phenyl]-propionic acid methyl ester, (E)-(S)-2-(2-Benzoyl-phenylamino)-3-[4-(3-quinolin-2-yl-allyloxy)-phenyl]-propionic acid, or or a salt thereof with a pharmaceutically acceptable acid or base, or any optical isomer or mixture of optical isomers, including a racemic mixture, or any tautomeric forms.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, guanidine and the like. Examples of cationic amino acids include lysine, arginine, histidine and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, aminoacids, aminoalcohols derived from aminoacids; conventional reaction conditions may be employed to convert acid into an amide; the dia-stereomers may be separated either by fractional crystallization or chromatography and the stereoisomers of compound of formula I may be prepared by hydrolysing the pure diastereomeric amide.

Various polymorphs of compound of general formula I forming part of this invention may be prepared by crystallization of compound of formula I under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Furthermore, the present compounds of formula I can be utilised in the treatment and/or prevention of conditions mediated by nuclear receptors, in particular the Peroxisome Proliferator-Activated Receptors (PPAR).

In a further aspect, the present invention relates to a method of treating and/or preventing Type I or Type II diabetes.

In a still further aspect, the present invention relates to the use of one or more compounds of the general formula I or pharmaceutically acceptable salts thereof for the preparation of a medicament for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, hyperlipidemia, coronary artery disease, myocardial ischemia and other cardiovascular disorders.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

The present compounds may also be administered in combination with one or more further pharmacologically active substances eg., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a biguanide eg. mefformin.

In yet another embodiment the present compounds are administered in combination with a meglitinide eg. repaglinide or senaglinide.

In a further embodiment the present compounds are administered in combination with an α-glucosidase inhibitor eg. miglitol or acarbose.

In another embodiment the present compounds are administered in combination with an agent acting on the ATP-dependent potassium channel of the β-cells eg. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds eg. in combination with a sulphonylurea and metformin, a sulphonylurea and acarbose, repaglinide and mefformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

Furthermore, the invention relates to the use of compounds of the general formula I or their tautomeric forms, their stereoisomers, their polymorphs, their pharmaceutically acceptable salts or pharmaceutically acceptable solvates thereof for the preparation of a pharmaceutical composition for the treatment and/or prevention of conditions mediated by nuclear receptors, in particular the Peroxisome Proliferator-Activated Receptors (PPAR) such as the conditions mentioned above.

The present invention also relates to a process for the preparation of the above said novel compounds, their derivatives, their analogs, their tautomeric forms, their stereoisomers, their polymorphs, their pharmaceutically acceptable salts or pharmaceutically acceptable solvates.

PHARMACEUTICAL COMPOSITIONS

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9–40 T approx. | 0.9 mg |

*Acylated monoglyceride used as plasticizer for film coating.

If desired, the pharmaceutical composition of the invention may comprise the compound of formula (I) in combination with further pharmacologically active substances such as those described in the foregoing.

The compounds of the invention may be administered to a mammal, especially a human in need of such treatment, prevention, elimination, alleviation or amelioration of diseases related to the regulation of blood sugar.

Such mammals include also animals, both domestic animals, e.g. household pets, and non-domestic animals such as wildlife.

The compounds of the invention are effective over a wide dosage range. A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg. Any novel feature or combination of features described herein is considered essential to this invention.

The present invention is further illustrated in the following representative examples which are, however, not intended to limit the scope of the invention in any way.

EXAMPLES

The compounds used as starting materials are either known compounds or compounds which can readily be prepared by methods known per se. The structures of the compounds are confirmed by either elemental analysis (MA) nuclear magnetic resonance (NMR), mass spectrometry (MS) or optical rotation. NMR shifts ($\delta$) are given in parts per million (ppm) and only selected peaks are given. mp is melting point and is given in ° C. Column chromatography was carried out using the technique described by W. C. Still et al, J. Org. Chem. 1978, 43, 2923–2925 on Merck silica gel 60 (Art 9385). The optical rotation was measured on a Advanced Laser Polarimeter.

The abbreviations as used in the examples have the following meaning:

| THF: | tetrahydrofuran |
|---|---|
| DMSO: | dimethylsulfoxide |
| $CDCl_3$: | deutorated chloroform |
| DMF: | N,N-dimethylformamide |
| min: | minutes |
| h: | hours |

General Procedure (A)

Step A:

Reacting a compound of formula II

(II)

wherein X and Y are defined as above, through a Wittig-like process with for example $(EtO)_2PO(CHR_1)COOR_5$ (wherein $R_5$ is an alkyl group), in the presence of a base such as sodium hydride, EtONa and the like to give a compound of formula III

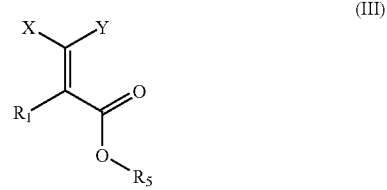
(III)

wherein X, Y, $R_1$ and $R_5$ are defined as above

Step B:

Reducing a compound of formula III, wherein X, Y, $R_1$ and $R_5$ are defined as above with a suitable reagent such as diisobutylaluminium hydride, to give a compound of formula IV

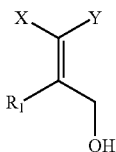

(IV)

wherein X, Y and R₁ are defined as above, and

Step C:

Reacting a compound of formula IV, wherein X, Y and R₁ are defined as above (except that when X or Y is substituted with hydroxy, amino, $C_{1-6}$-alkylamino or $C_{2-6}$-dialkylamino these functionalities have to be protected) with a compound of formula V

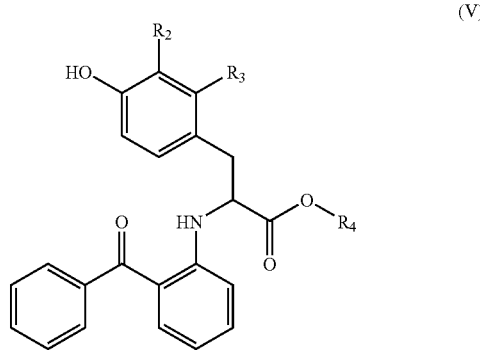

(V)

wherein R₂, R₃, and R₄ are defined as above, except that R₄ is not hydrogen under Mitsunobu conditions, using a reagent such as triphenylphosphine/diethylazodicarboxylate and the like to obtain a compound of formula I, or a protected for hereof, wherein X, Y, R₁, R₂, R₃ and R₄ are defined as above, except that R₄ is not hydrogen.

General Procedure (B)

Step A:

Converting the —OH functionality in a compound of formula IV, wherein X, Y and R₁ are defined as above, to an appropriate leaving group (L) such as p-toluenesulfonate, methanesulfonate, halogen (for example by methods according to: Houben-Weyl, Methoden der organischen Chemie, Alkohole III, 6/1b, Thieme-Verlag 1984, 4th Ed., pp. 927–939; Comprehensive Organic Transformations. A guide to functional group preparations, VCH Publishers 1989, 1$^{st}$ Ed., pp. 353–363 and *J. Org. Chem.*, Vol. 36 (20), 3044–3045, 1971), triflate and the like, to give a compound of formula VI

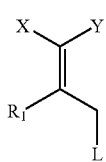

(VI)

wherein X, Y, R₁ and L are defined as above.

Step B:

Reacting a compound of formula VI wherein L is a leaving group such as p-toluenesulfonate, methanesulfonate, halogen, triflate and the like and wherein X, Y and R₁ are defined as above with a compound of formula V wherein R₂, R₃, and R₄ are defined as above, except that R₄ is not hydrogen to give a compound of formula I wherein X, Y, R₁, R₂, R₃ and R₄ are defined as above, except that R₄ is not hydrogen.

General Procedure (C)

Step A:

By chemical or enzymatic saponification of a compound of formula I wherein X, Y, R₁, R₂, R₃ and R₄ are defined as above, except that R₄ is not hydrogen to give a compound of formula I wherein X, Y, R₁, R₂, R₃ and R₄ are defined as above, except that R₄ is hydrogen.

Example 1

General Procedure (A)

(E)-(S)-2-(2-Benzoyl-phenylamino)-3-[4-(3-biphenyl-4-yl-allyloxy)-phenyl]-propionic acid methyl ester

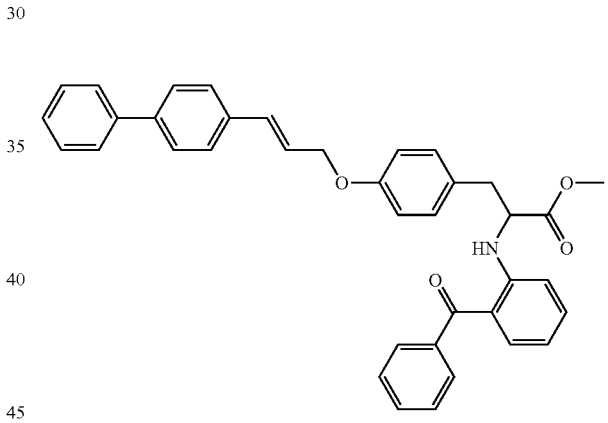

Step C:

Under an atmosphere of nitrogen, azodicarboxylic dipiperidide (620 mg, 2.5 mmol) was added at 0–5° C. to a stirred solution of (S)-2-(2-benzoyloxy-phenylamino)-3-(4-hydroxyphenyl)-propionic acid methyl ester (470 mg, 1.25 mmol), (E)-3-(4-biphenylyl)-2-propen-1-ol (260 mg, 1.25 mmol) and tributylphosphine (500 mg, 2.5 mmol) in dry THF (50 ml). The mixture was stirred over night. The reaction mixture was diluted with water and the product extracted with ethyl acetate. The organic layers were combined, washed with water, dried (MgSO₄) and evaporated. The crude product was then purified by column chromatography on silica (eluent: 25% ethyl acetate in heptane) to give 420 mg (60%) of the title compound.

¹H NMR (CDCL₃): δ3.12 (1H, dd), 3.23 (1H, dd), 3.68 (3H, s), 4.40 (1H, q), 4.65.(2H, d), 6.40 (1H, dt), 6.55 (1H, t), 6.65 (1H, d), 6.73 (1H, d), 6.90 (2H, d), 7.20 (2H, d), 7.32 (2H, t), 7.35–7.50 (8H, m), 7.50–7.63 (6H, m), 8.93 (1H, d).

Example 2

General Procedure (C)

(E)-(S)-2-(2-Benzoyl-phenylamino)-3-[4-(3-biphenyl-4-yl-allyloxy)-phenyl]-propionic acid

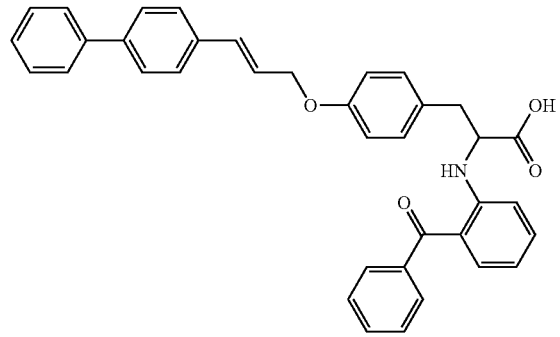

Step A:

(E)-(S)-2-(2-Benzoyl-phenylamino-3-[4-(3-biphenyl-4-yl-allyloxy)-phenyl]-propionic acid methyl ester (example 1) (400 mg, 0.7 mmol) was dissolved in a mixture of ethanol (15 ml) and THF (15 ml). 1N NaOH (3 ml) was added and the mixture was stirred for 1 h at room temperature. The mixture was concentrated in vacuo. Water (5 ml) and ethyl acetate (10 ml) was added. The mixture was neutralised with 1N HCl. The aqueous phase was isolated and extracted with ethyl acetate (×2) The organic layers were combined, washed with water, dried (MgSO$_4$) and evaporated to give 400 mg of the title compound.

$^1$H NMR (CDCl$_3$): δ 3.15 (1H, dd), 3.30 (1H, dd), 4.40 (1H, bs), 4.64 (2H, d), 6.42 (1H, dt), 6.57–6.77 (3H, m), 6.88 (2H, d), 7.23 (2H, d), 7.30–7.62 (17H, m), 8.88 (1H, bs).

Example 3

General Procedure (A)

(E)-(S)-2-(2-Benzoyl-phenylamino)-3-{4-[3-(9H-fluoren-2-yl)-allyloxy]-phenyl}-propionic acid methyl ester

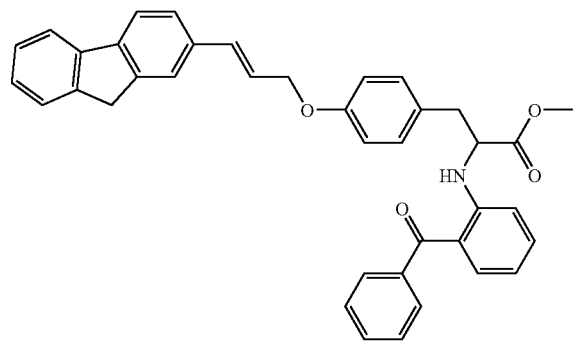

Step A:

Triethyl phosphonoacetate (16.8 g, 75.0 mmol) was added at 0° C. over a period of 10 min. to a stirred suspension of sodium hydride (60% in oil, 2.05 g, 51.5 mmol) in dry toluene (200 mL). After stirring at 0° C. for 15 min. a solution of fluorine-2-carboxaldehyde (9.7 g, 50.0 mmol) in dry toluene/THF (1:1) (50 mL). After adding THF (100 ml), the mixture was slowly warmed to room temperature, and stirring continued for 24 h. The reaction mixture was quenched with ethanol (50 ml) and added water (300 ml). The aqueous phase was separated and further extracted with ethyl acetate (250 mL). The combined organic phases were washed with water (300 mL), dried (MgSO$_4$), filtered and concentrated in vacuo. The product was purified by flash column chromatography to give 13.0 g (E)-3-(9H-fluoren-2-yl)-acrylic acid ethyl ester.

$^1$H NMR (CDCl$_3$): δ 1.37 (2H, t), 3.92 (2H, s), 4.28 (2H, q), 6.47 (1H, d), 7.30–7.42 (2H, m), 7.55 (2H, d), 7.68–7.82 (4H, m).

Step B:

Under an atmosphere of nitrogen a 1M solution of DIBAL-H in toluene (80 ml, 80 mmol) was added dropwise at −70° C. over 20 min. to a stirred solution of (E)-3-(9H-fluoren-2-yl)-acrylic acid ethyl ester (5.3 g, 20.0 mmol) in dry THF (150 ml) and the mixture stirred for 30 min. Methanol (2 ml) was added, followed by saturated aqueous Rochelle's salt (100 ml), and 1N NaOH. The aqueous phase was separated and further extracted with dichloromethane. The combined organic phases were washed with water (300 mL), dried (MgSO$_4$), filtered and concentrated in vacuo yielding 4.1 g (92%) of (E)-3-(9H-fluoren-2-yl)-prop-2-en-1-ol.

$^1$H NMR (CDCl$_3$): δ 1.48 (1H, s), 3.90 (2H, s), 4.35 (2H, s), 6.42 (1H, dt), 6.70 (1H, d), 7.25–7.45 (3H, m), 7.53 (1H, d), 7.58 (1H, s), 7.73 (1H, d), 7.77 (1H, d).

Step C:

Under an atmosphere of nitrogen, azodicarboxylic dipiperidide (1.21 g, 6.0 mmol) was added at 0–5° C. to a stirred solution of (S)-2-(2-benzoyloxy-phenylamino)-3-(4-hydroxyphenyl)-propionic acid methyl ester (1.13 g, 3.0 mmol), (E)-3-(9H-fluoren-2-yl)-prop-2-en-1-ol (670 mg, 3.0 mmol) and tributylphosphine (1.5 g, 6.0 mmol) in dry THF (100 ml). The mixture was stirred over night. The reaction mixture was concentrated in vacuo, diluted with water and the product extracted with ethyl acetate. The organic layers were combined, washed with water, dried (MgSO$_4$) and evaporated. The crude product was then purified by column chromatography on silica (eluent: 25% ethyl acetate in heptane) to give 1.0 g (57%) of the title compound.

Example 4

General Procedure (C)

(E)-(S)-2-(2-Benzoyl-phenylamino)-3-{4-[3-(9H-fluoren-2-yl)-allyloxy]-phenyl}-propionic acid

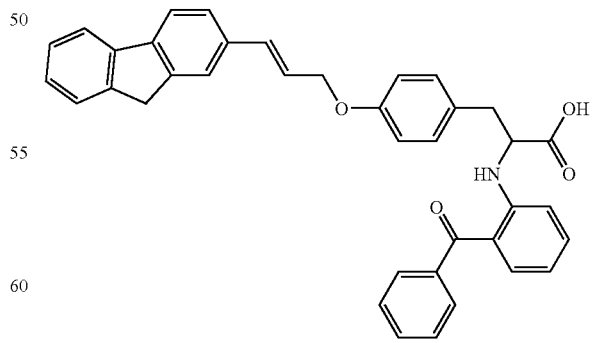

Step A:

(E)-(S)-2-(2-Benzoyl-phenylamino)-3-{4-[3-(9H-fluoren-2-yl)-allyloxy]-phenyl}-propionic acid methyl ester (example 3) (600 mg, 1.0 mmol) was dissolved in a mixture of ethanol (20 ml) and THF (10 ml). 1N NaOH (5 ml) was added and the mixture was stirred for 16 h at room temperature. The mixture was concentrated in vacuo. Water (5 ml) and ethyl acetate (10 ml) was added. The mixture was neutralised with 1N HCl. The aqueous phase was isolated and extracted with ethyl acetate (×2) The organic layers were combined, washed with water, dried (MgSO$_4$) and evaporated to give 500 mg of the title compound.

$^1$H NMR (CDCl$_3$): δ 3.17 (1H, dd), 3.30 (1H, dd), 3.87 (2H, s), 4.40 (1H, bs), 4.66 (2H, d), 6.42 (1H, dt), 6.54 (2H, dd), 6.77 (2H, d), 6.90 (2H, d), 7.23 (2H, d), 7.28–7.63 (11H, m), 7.73 (2H, dd), 8.85 (1H, bs).

Example 5

General Procedure (A)

(S)-2-(2-Benzoyl-phenylamino)-3-{4-[2-ethyl-3-(9H-fluoren-2-yl)-allyloxy]-phenyl}-propionic acid methyl ester.

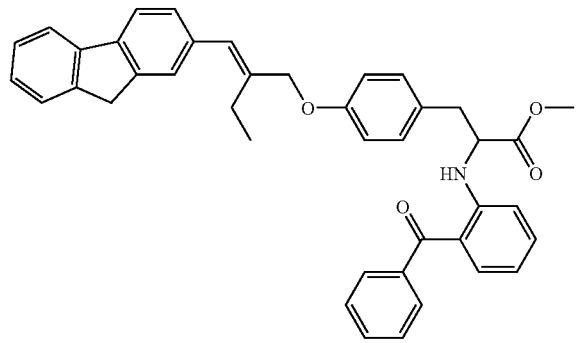

Step A:

A solution of triethyl-2-phosphonobutyrate (5.7 g, 22.6 mmol) in dry THF (10 ml) was added at 0° C. over a period of 10 min. to a stirred suspension of sodium hydride (60% in oil, 800 mg, 20.0 mmol) in dry THF (15 mL). After stirring at 0° C. for 30 min. a solution of fluorene-2-carboxaldehyde (2.5 g, 12.8 mmol) in dry THF (15 mL). The mixture was slowly warmed to room temperature, and stirring continued for 24 h. The reaction mixture was quenched with 1 N HCl (40 ml) and the product extracted with ethyl acetate (×2). The combined organic phases dried (MgSO$_4$), filtered and concentrated in vacuo. The residue was suspended in heptane and 2-ethyl-3-(9H-fluoren-2-yl)-acrylic acid ethyl ester isolated by filtration.

$^1$H NMR (CDCl$_3$): δ 1.22 (3H, t), 1.37 (3H, t), 2.62 (2H, q), 3.92 (2H, s), 4.29 (2H, q), 7.28–7.40 (2H, m), 7.42 (1H, d), 7.55 (1H, d), 7.57 (1H, s), 7.73 (1H, s), 7.80 (2H, d).

Step B:

Under an atmosphere of nitrogen a 1M solution of DIBAL-H in toluene (10.5 ml, 10.5 mmol) was added dropwise at −70° C. over 20 min. to a stirred solution of 2-ethyl-3-(9H-fluoren-2-yl)-acrylic acid ethyl ester (1.54 g, 5.3 mmol) in dry THF (75 ml) and the mixture stirred for 45 min. Methanol (2 ml) was added, followed by 1N HCl and ethyl acetate. The aqueous phase was separated and further extracted with ethyl acetate. The combined organic phases were washed with water, dried (MgSO$_4$), filtered and concentrated in vacuo yielding 1.3 g of 2-ethyl-3-(9H-fluoren-2-yl)-prop-2-en-1-ol.

$^1$H NMR (CDCl$_3$): δ 1.17 (3H, t), 1,57 (1H, bs), 2.42 (2H, q), 3.90 (2H, s), 4.28 (2H, d), 6.60 (1H, s), 7.25–7.32 (2H, m), 7.38 (1H, t), 7.45 (1H, s), 7.54 (1H, d), 7.77 (1H, t).

Step C:

Under an atmosphere of nitrogen, azodicarboxylic dipiperidide (610 mg, 2.4 mmol) was added at 0–5° C. to a stirred solution of (S)-2-(2-benzoyloxy-phenylamino)-3-(4-hydroxyphenyl)-propionic acid methyl ester (450 mg, 1.2 mmol), 2-ethyl-3-(9H-fluoren-2-yl)-prop-2-en-1-o (300 mg, 1.2 mmol) and tributylphosphine (490 mg, 2.4 mmol) in dry THF (50 ml). The mixture was stirred for 1.5 h. The reaction mixture was concentrated in vacuo, diluted with water and the product extracted with ethyl acetate. The organic layers were combined, washed with water, dried (MgSO$_4$) and evaporated. The crude product was then purified by column chromatography on silica (eluent: 75% ethyl acetate in heptane) to give 700 mg of the title compound.

$^1$H NMR (CDCL$_3$): δ 1.17 (3H, t), 2.45 (2H, q), 3.12 (1H, dd), 3.23 (1H, dd), 3.68 (3H, s), 3.88 (2H, s), 4.40 (1H, q), 4.58 (2H, s), 6.55 (1H, t), 6.63 (1H, d), 6.65 (1H, s), 6.90 (2H, d), 7.20 (2H, d), 7.23–7.35 (4H, m), 7.35–7.54 (6H, m), 7.60 (2H, d), 7.74 (2H, t), 8.94 (1H, d).

Example 6

General Procedure (C)

(S)-2-(2-Benzoyl-phenylamino)-3-{4-[2-ethyl-3-(9H-fluoren-2-yl)-allyloxy]-phenyl}-propionic acid.

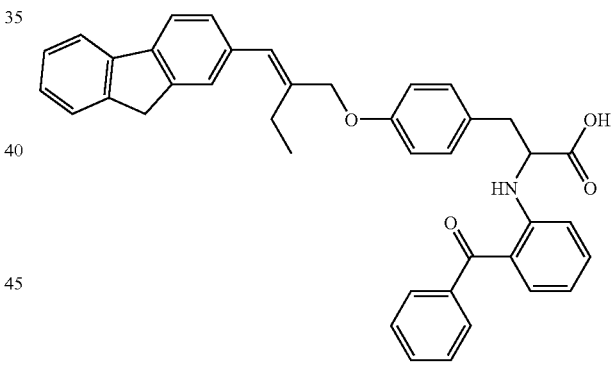

Step A:

(S)-2-(2-Benzoyl-phenylamino)-3-{4-[2-ethyl-3-(9H-fluoren-2-yl)-allyloxy]-phenyl}-propionic acid methyl ester (example 5) (700 mg, 1.15 mmol) was dissolved in a mixture of ethanol (20 ml) and THF (20 ml). 1N NaOH (10 ml) was added and the mixture was stirred for 16 h at 5° C. The mixture was concentrated in vacuo. 1N HCl and ethyl acetate (10 ml) was added. The aqueous phase was isolated and extracted with ethyl acetate (×2) The organic layers were combined, washed with water, dried (MgSO$_4$) and evaporated to give 500 mg of the title compound.

$^1$H NMR (CDCl$_3$): δ 1.05 (3H, t), 2.32 (2H, q), 2.85 (1H, dd), 3.14 (1H, dd), 3.80 (2H, s), 4.20 (1H, bs), 4.30 (2H, s), 6.34 (1H, t), 6.42 (1H, d), 6.48 (1H, s), 6.67 (2H, d), 6.98–7.12 (3H, m), 7.15–7.40 (9H, m), 7.47 (3H, d), 7.65 (1H, d), 7.70 (1H, d).

Example 7

General Procedure (A)

(E)-(S)-2-(2-Benzoyl-phenylamino)-3-[4-(3-quinolin-2-yl-allyloxy)-phenyl]-propionic acid methyl ester

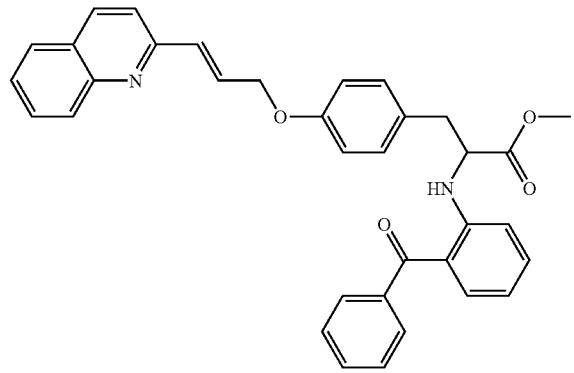

Step A:

A solution of triethyl-2-phosphonobutyrate (26.6 g, 118.7 mmol) in dry toluen (250 ml) was cooled on ice and added sodium hydride (60% in oil, 3.3 g, 134.6 mmol). After stirring at 0° C. for 20 min. a solution of quinolinecarboxaldehyde (12.5 g, 79.5 mmol) in dry THF (30 mL) was added. The mixture was slowly warmed to room temperature, and stirring continued for 24 h. The reaction mixture was quenched with ethanol and added water. The aqueous phase was extracted with dichloro methane (×2). The combined organic phases were dried (MgSO$_4$), filtered and concentrated in vacuo. The residue was submitted to flash chromatography, eluting with heptane graduated to heptane/ethyl acetate (4:1), to give 12.5 g (70%) of (E)-3-quinolin-2-yl-acrylic acid ethyl ester.

$^1$H NMR (CDCl$_3$): δ 1.37 (3H, t), 4.30 (2H, q), 6.98 (1H, d), 7.55 (1H, t), 7.62 (1H, d), 7.75 (1H, t), 7.83 (1H, d), 7.91 (1H, d), 8.10 (1H, d), 8.19 (1H, d).

Step B:

Under an atmosphere of nitrogen a 1M solution of DIBAL-H in toluene (82 ml, 82 mmol) was added dropwise at −70° C. over 20 min. to a stirred solution of (E)-3-quinolin-2-yl-acrylic acid ethyl ester (12.5 g, 55 mmol) in dry THF (400 ml) and the mixture stirred for 3 h. Methanol (100 ml) was added, and the mixture was concentrated in vacuo. The residue was dissolved in 1N HCl (500 mL) and ethyl acetate (100 mL). The aqueous phase was separated and added 1 N NaOH to pH 8. The product was extracted with dichloromethane. The combined organic phases were washed with water, dried (MgSO$_4$), filtered and concentrated in vacuo. The residue was dissolved in ethyl acetate, treated with activated charcoal, filtered, and concentrated in vacuo yielding 5.6 g (56%) of (E)-3-quinolin-2-yl-prop-2-en-1-ol.

$^1$H NMR (CDCl$_3$): δ 4.32 (1H, bs), 4.45 (2H, d), 6.88 (1H, dt), 7.04 (1H, d), 7.45–7.53 (2H, m), 7.64–7.75 (2H, m), 8.03 (1H, d), 8.08 (1H, d).

Step C:

Under an atmosphere of nitrogen, azodicarboxylic dipiperidide (504 mg, 2.0 mmol) was added at 0–5° C. to a stirred solution of (S)-2-(2-benzoyloxy-phenylamino)-3-(4-hydroxyphenyl)-propionic acid methyl ester (300 mg, 0.8 mmol), (E)-3-quinolin-2-yl-prop-2-en-1-ol (185 mg, 1.0 mmol) and tributylphosphine (404 mg, 2.0 mmol) in dry THF (30 ml). The mixture was stirred for 1.5 h. The reaction mixture was concentrated in vacuo, diluted with water and the product extracted with ethyl acetate. The organic layers were combined, washed with water, dried (MgSO$_4$) and evaporated. The crude product was purified by column chromatography on a CN-column, eluting with acetonitrile+0.1% TFA graduated with from 20–100% water+0.1% TFA. The title compound was isolated in 100 mg yield.

MS: 443 (M$^+$, 100%), 272.

Example 8

General Procedure (C)

(E)-(S)-2-(2-Benzoyl-phenylamino)-3-[4-(3-quinolin-2-yl-allyloxy)-phenyl]-propionic acid

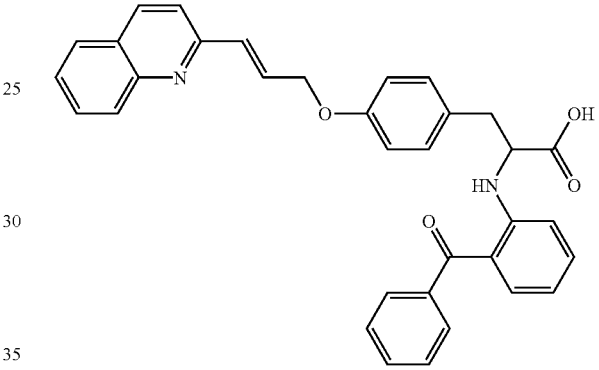

Step A:

(E)-(S)-2-(2-Benzoyl-phenylamino)-3-[4-(3-quinolin-2-yl-allyloxy)-phenyl]-propionic acid methyl ester (example 7) (100 mg, 0.18 mmol) was dissolved in ethanol (10 ml). 1N NaOH (3 ml) was added and the mixture was stirred for 16 h at room temperature. The mixture was concentrated in vacuo. 1N HCl and ethyl acetate (10 ml) was added. The aqueous phase was isolated and extracted with ethyl acetate (×2) The organic layers were combined, washed with water, dried (MgSO$_4$) and evaporated. The product was purified on a reverse phase column eluting with acetonitrile.

MS: 529 (M$^+$, 100%), 265.

Pharmacological Methods

In Vitro PPARalpha, PPARgamma and PPARdelta Activation Activity

The PPAR transient transactivation assays are based on transient transfection into human HEK293 cells of two plasmids encoding a chimeric test protein and a reporter protein respectively. The chimeric test protein is a fusion of the DNA binding domain (DBD) from the yeast GAL4 transcription factor to the ligand binding domain (LBD) of the human PPAR proteins. The PPAR-LBD moiety harbored in addition to the ligand binding pocket also the native activation domain (activating function 2=AF2) allowing the fusion protein to function as a PPAR ligand dependent transcription factor. The GAL4 DBD will direct the chimeric protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand luciferase protein will be produced in amounts corresponding to the activation of the PPAR protein. The amount of luciferase protein is measured by light emission after addition of the appropriate substrate.

Cell Culture and Transfection

HEK293 cells were grown in DMEM+10% FCS. Cells were seeded in 96-well plates the day before transfection to give a confluency of 50–80% at transfection. A total of 0.8 μg DNA containing 0.4 μg pM1α/γLBD, 0.1 μg pCMVβGal, 0.08 μg pGL2(Gal4)₅ and 0.02 μg pADVANTAGE was transfected per well using FuGene transfection reagent according to the manufacturers instructions (Roche). Cells were allowed to express protein for 48 h followed by addition of compound.

Plasmids: Human PPAR α, γ and δ was obtained by PCR amplification using cDNA synthesized by reverse transcription of mRNA from human liver, adipose tissue and placenta respectively. Amplified cDNAs were cloned into pCR2.1 and sequenced. The ligand binding domain (LBD) of each PPAR isoform was generated by PCR (PPARα: aa 167—C-terminus; PPARγ: aa 165—C-terminus; PPARδ: aa 128—C-terminus) and fused to the DNA binding domain (DBD) of the yeast transcription factor GAL4 by subcloning fragments in frame into the vector pM1 (Sadowski et al. (1992), Gene 118, 137) generating the plasmids pM1αLBD, pM1γLBD and pM1δ. Ensuing fusions were verified by sequencing. The reporter was constructed by inserting an oligonucleotide encoding five repeats of the GAL4 recognition sequence (5×CGGAGTACTGTCCTCCG(AG)) (Webster et al. (1988), Nucleic Acids Res. 16, 8192) into the vector pGL2 promotor (Promega) generating the plasmid pGL2(GAL4)₅. pCMVβGal was purchased from Clontech and pADVANTAGE was purchased from Promega.

In Vitro Transactivation Assay

Compounds: All compounds were dissolved in DMSO and diluted 1:1000 upon addition to the cells. Compounds were tested in quadruple in concentrations ranging from 0.001 to 300 μM. Cells were treated with compound for 24 h followed by luciferase assay. Each compound was tested in at least two separate experiments.

Luciferase assay: Medium including test compound was aspirated and 100 μl PBS incl. 1 mM Mg++ and Ca++ was added to each well. The luciferase assay was performed using the LucLite kit according to the manufacturers instructions (Packard Instruments). Light emission was quantified by counting on a Packard LumiCounter. To measure β-galactosidase activity 25 μl supernatant from each transfection lysate was transferred to a new microplate. β-galactosidase assays were performed in the microwell plates using a kit from Promega and read in a Labsystems Ascent Multiscan reader. The β-galactosidase data were used to normalize (transfection efficiency, cell growth etc.) the luciferase data.

Statistical Methods

The activity of a compound is calculated as fold induction compared to an untreated sample. For each compound the efficacy (maximal activity) is given as a relative activity compared to to Wy14,643 for PPARα, Rosiglitazone for PPARγ and Carbacyclin for PPARδ. The EC50 is the concentration giving 50% of maximal observed activity. EC50 values were calculated via non-linear regression using GraphPad PRISM 3.02 (GraphPad Software, San Diego, Calif.). The results were expressed as means±SD.

The invention claimed is:

1. A compound of formula (I)

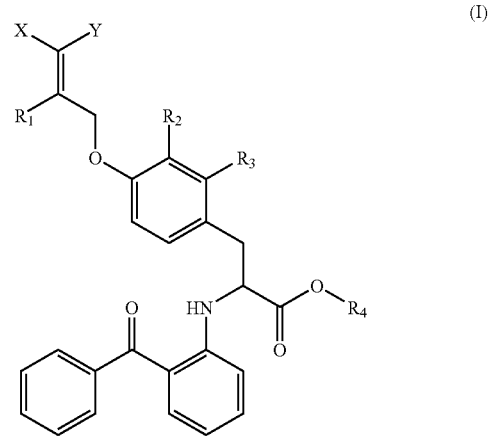

wherein X is biphenyl, a fused polycyclic hydrocarbon, or heteroaryl, each of which is optionally substituted with one or more substituents selected from the group consisting of:
halogen, perhalomethyl, perhalomethoxy, hydroxy, cyano, amino, $C_{1-6}$-alkylamino, $C_{3-6}$-cycloalkylamino, $C_{1-6}$-dialkylamino, or carboxy;
$C_{1-6}$-alkyl, $C_{3-6}$-cycloalkyl, $C_{2-6}$-alkenyl, $C_{2-6}$-alkynyl, $C_{1-6}$-alkoxy, $C_{3-6}$-cycloalkoxy, $C_{1-6}$-alkylthio, or $C_{3-6}$-cycloalkylthio, each of which is optionally substituted with halogen; and wherein
Y is H, $C_{1-6}$-alkyl, $C_{3-6}$-cycloalkyl, $C_{2-6}$-alkenyl, $C_{2-6}$-alkynyl, or $C_{4-6}$-alkenynyl; and
$R_1$ is hydrogen or halogen; or
$R_1$ is $C_{1-6}$-alkyl, $C_{3-6}$-cycloalkyl, $C_{1-6}$-alkoxy or $C_{3-6}$-cycloalkoxy, each of which is optionally substituted with one or more substituents selected from the group consisting of halogen, hydroxy, and cyano; and
$R_2$ and $R_3$ are independently hydrogen, halogen, $C_{1-6}$-alkyl or $C_{3-6}$-cycloalkyl; and
$R_4$ is hydrogen, $C_{1-6}$-alkyl or $C_{3-6}$-cycloalkyl; or
a pharmaceutically acceptable salt thereof, or a pharmaceutically acceptable solvate thereof, or any tautomeric forms, stereoisomers, mixture of stereoisomers including a racemic mixture, or polymorphs.

2. A compound according to claim 1 wherein X is biphenyl, a fused polycyclic hydrocarbon or heteroaryl each of which is optionally substituted with one or more substituents selected from the group consisting of:
halogen; and
$C_{1-6}$-alkyl or $C_{1-6}$-alkoxy, each of which is optionally substituted with halogen.

3. A compound according to claim 1, wherein X is biphenyl optionally substituted with one or more substituents selected from the group consisting of:
halogen; and
$C_{1-6}$-alkyl or $C_{1-6}$-alkoxy, each of which is optionally substituted with halogen.

4. A compound according to claim 1, wherein X is a fused polycyclic hydrocarbon optionally substituted with one or more substituents selected from the group consisting of:

halogen; and
C$_{1-6}$-alkyl or C$_{1-6}$-alkoxy, each of which is optionally substituted wit halogen.

5. A compound according to claim 1, wherein X is heteroaryl optionally substituted with one or more substituents selected from
halogen; or
C$_{1-6}$-alkyl or C$_{1-6}$-alkoxy each of which is optionally substituted with halogen.

6. A compound according to claim 1, wherein X is biphenyl.

7. A compound according to claim 4, wherein X is fluorenyl.

8. A compound according to claim 5, wherein X is quinolyl.

9. A compound according to claim 1, wherein Y is H.

10. A compound according to claim 1, wherein Y is C$_{1-6}$-alkyl optionally substituted with one or more halogens.

11. A compound according to claim 1, wherein R$_1$ is H or C$_{1-6}$-alkyl.

12. A compound according to claim 1, wherein R$_2$ is hydrogen.

13. A compound according to claim 1, wherein R$_3$ is hydrogen.

14. A compound according to claim 1, wherein R$_1$ is hydrogen or C$_{1-6}$-alkyl.

15. A compound according to claim 14, wherein R$_4$ is hydrogen or methyl.

16. A compound according to claim 1, wherein said compound is selected from the group consisting of:
- (E)-(S)-2-(2-Benzoyl-phenylamino)-3-[4-(3-biphenyl-4-yl-allyloxy)-phenyl]-propionic acid methyl ester,
- (E)-(S)-2-(2-Benzoyl-phenylamino)-3-[4-(3-biphenyl-4-yl-allyloxy)-phenyl]-propionic acid,
- (E)-(S)-2-(2-Benzoyl-phenylamino)-3-{4-[3-(9H-fluoren-2-yl)-allyloxyl]-phenyl}-propionic acid methyl ester,
- (E)-(S)-2-(2-Benzoyl-phenylamino)-3-{4-[3-(9H-fluoren-2-yl)-allyloxy]-phenyl}-propionic acid,
- (S)-2-(2-Benzoyl-phenylamino)-3-{4-[2-ethyl-3-(9H-fluoren-2-yl)-allyloxy]-phenyl}-propionic acid methyl ester,
- (S)-2-(2-Benzoyl-phenylamino)-3-{4-[2-ethyl-3-(9H-fluoren-2-yl)-allyloxy]-phenyl}-propionic acid,
- (E)-(S)-2-(2-Benzoyl-phenylamino)-3-[4-(3-quinolin-2-yl-allyloxy)-phenyl]-propionic acid methyl ester, and
- (E)-(S)-2-(2-Benzoyl-phenylamino)-3-[4-(3-quinolin-2-yl-allyloxy)-phenyl]-propionic acid, or a pharmaceutically acceptable salt thereof.

17. A pharmaceutical composition comprising, as an active ingredient, at least one compound according to claim 1 and one or more pharmaceutically acceptable carriers or excipients.

18. A pharmaceutical composition according to claim 17 in unit dosage form, comprising from about 0.05 mg to about 1000 mg of said compound.

19. A pharmaceutical composition according to claim 17 for oral, nasal, transdermal, pulmonal, or parenteral administration.

20. A method for the treatment of type I diabetes, type II diabetes, impaired glucose tolerance, insulin resistance or obesity, the method comprising administering to a subject in need thereof an effective amount of a compound according to claim 1.

21. A method for the treatment of type I diabetes, type II diabetes, impaired glucose tolerance, insulin resistance or obesity, the method comprising administering to a subject in need thereof an effective amount of the pharmaceutical composition of claim 17.

* * * * *